US007357951B2

(12) United States Patent
Koyama et al.

(10) Patent No.: US 7,357,951 B2
(45) Date of Patent: Apr. 15, 2008

(54) COMPOSITION FOR PREVENTING ATHEROSCLEROSIS

(75) Inventors: Naoto Koyama, Kawasaki (JP); Kanna Kuribayashi, Kawasaki (JP); Koichi Ishii, Kawasaki (JP); Katsunori Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/960,919

(22) Filed: Oct. 12, 2004

(65) Prior Publication Data
US 2005/0136137 A1 Jun. 23, 2005

Related U.S. Application Data

(63) Continuation of application No. PCT/JP03/04607, filed on Apr. 11, 2003.

(30) Foreign Application Priority Data
Apr. 12, 2002 (JP) ............................. 2002-110932

(51) Int. Cl.
*A61K 36/286* (2006.01)
(52) U.S. Cl. ...................... 424/776; 514/415
(58) Field of Classification Search ...................... None
See application file for complete search history.

(56) References Cited

U.S. PATENT DOCUMENTS

| | | | | |
|---|---|---|---|---|
| 4,244,973 A | * | 1/1981 | van Megen | 426/49 |
| 4,265,925 A | * | 5/1981 | Campbell et al. | 426/641 |
| 4,418,064 A | * | 11/1983 | Powell et al. | 514/229.5 |
| 5,635,193 A | * | 6/1997 | Walter et al. | 424/405 |

FOREIGN PATENT DOCUMENTS

| | | |
|---|---|---|
| EP | 1 052 283 A1 | 11/2000 |
| JP | 63-276450 | 11/1988 |
| JP | 7-188044 | 7/1995 |
| JP | 2001-158726 | 6/2001 |
| JP | 2003-88334 | 3/2003 |
| WO | WO 00/57898 | 10/2000 |
| WO | WO 02/22146 A2 | 3/2002 |

OTHER PUBLICATIONS http://www.americanheart.org/presenter.jhtml?identifier=4704; accessed Dec. 6, 2005.*
CAPLUS English abstract of KR 2001034952 (2001).*
Kang et al. (J. Food Sci. Nutr. (1999), vol. 4, No. 4, pp. 221-225).*
English translation of KR 2001034952 (2001).*
S. Huard, et al., "Effects of Mechanical Treatment of Whole Canola Seeds on Carcass Composition and Blood Lipids of Lambs Fed Grass Silage", Canadian Journal of Animal Science, vol. 78, No. 4, 1998, pp. 665-671.
Kwang-Deog Moon, et al., "Safflower Seed Extract Lowers Plasma and Hepatic Lipids in Rats Fed High-Cholesterol Diet", Nutrition Research, 21, 2001, pp. 895-904.
H.L. Zhang, et al., "Antioxidative Compounds Isolated From Safflower (*Carthamus Tinctorius L.*) Oil Cake", Chem. Pharm. Bull., vol. 45, No. 12, 1997, pp. 1910-1914.
J. Fruebis, et al., "Extent of Antioxidant Protection of Plama LDL is Not a Predictor of the Antiatherogenic Effect of Antioxidants", Journal of Lipid Research, vol. 38, 1997, pp. 2455-2464.
J. Fruebis, et al., "Effect of Vitamin E on Atherogenesis in LDL Receptor-Deficient Rabbits", Atherosclerosis, 117, 1995, pp. 217-224.
J.S. Munday, et al., "Dietary Antioxidants Do Not Reduce Fatty Streak Formation in the C57BL/6 Mouse Atherosclerosis Model", Artherioscler. Thromb. Vasc. Biol., 18, 1998, pp. 114-119.
M. Wågberg, et al., 'N, N'-Diacetyl-L-Cystine (Dinac), The Disulphide Dimer of N-Acetylcysteine, Inhibits Atherosclerosis in WHHL Rabbits: Evidence for Immunomodulatory Agents as a New Approach to Prevent Atherosclerosis, The Journal of Pharmacology and Experimental Therapeutics, vol. 299, No. 1, 2001, pp. 76-82.
FASEB Journal, (Mar. 22, 2002), 16(5), pp. A1011; Biosis [on lin] STN, AN. 2002:370314, DN. PREV200200370314.
W.-O. Park, et al., "A Nutritional Study on Various Defatted Oil-Seed Flours and Mixtures", Korean J. Food Sci. Technol., vol. 6, No. 3, 1974, pp. 138-146.
S.-H. Cho, et al., "Effects of Defatted Safflower Seed Extracts on Plasma and Liver Lipid in Ovariectomized Female Rats Fed High Cholesterol Diets", Faseb Journal, vol. 16, No. 5, Mar. 22, 2002, p. A1011, XP-008047762.

* cited by examiner

*Primary Examiner*—Susan Coe Hoffman
(74) *Attorney, Agent, or Firm*—Oblon, Spivak, McClelland, Maier & Neustadt, P.C.

(57) ABSTRACT

The present invention provides a composition obtained by organic solvent extraction of defatted plant seed which is an atherosclerosis preventative agent. The present invention further provides a food and a pharmaceutical composition containing the composition, as well as a method of preventing an atherosclerotic disease.

10 Claims, 5 Drawing Sheets

(* rapeseed meal and safflower meal were 200-fold diluted while others were 50-fold diluted)

(a)

(b)

(c)

(a-1)

(b-1)

(c-1)

COMPOSITION FOR PREVENTING ATHEROSCLEROSIS

CROSS-REFERENCE TO RELATED APPLICATIONS

The present application is a continuation of International Application PCT/JP03/04607, filed on Apr. 11, 2003, which claims priority to Japanese application JP 2002-110932, filed on Apr. 12, 2002, the entire contents of these applications is incorporated herein by reference in their entirety.

BACKGROUND OF THE INVENTION

1. Field of the Invention

The present invention provides a composition obtained by organic solvent extraction of defatted plant seed which is an atherosclerosis preventative agent. The present invention further provides a food and a pharmaceutical composition containing the composition, as well as a method of preventing an atherosclerotic disease.

2. Discussion of the Background

Along with the westernization of life style in recent years, in addition to cancer, atherosclerotic diseases such as angina pectoris, intermittent claudication, cardiac infarction, cerebral infarction and the like have become the main causes of death of Japanese people. Once developed, these diseases are very difficult to cure, and dramatically degrade "quality of life." It is undisputable that a countermeasure to prevent or control the progression of atherosclerotic diseases is extremely important from a social standpoint as well.

A consensus has been generally reached that oxidation of low density lipoprotein (LDL) plays a key role in the early stages of lesion formation. As such, the importance of not only controlling the blood cholesterol level to a suitable range but also suppressing the production of oxidized LDL has been recently noted. It has been determined that certain foods, particularly a food derived from plants, contain an abundance of anti-oxidative substances. To this end, the anti-oxidative substances contained in green tea and red wine are considered to be taken into LDL (or in the vicinity thereof) and eliminate radical to prevent production of oxidized LDL (Fuhrman et al, Am. J. Clin. Nutr., 61: pp 549-54, 1995). There is also an epidemiological study that concludes that positive intake of these foods suppress cancer and heart diseases (Renaud et al, Lancet, 339: pp 1523-26, 1992).

In the meantime, there is a report that particular components derived from particular seeds such as sesame seed lignan, grapeseed polyphenol and the like show an anti-atherosclerotic activity with experimental animals (Kang et al, J. Nutr., 129: pp 1885-90, 1999; Yamakoshi et al, Atherosclerosis 142: pp 139-49, 1999). However, the anti-atherosclerotic property of a plant seed component has only been determined at an animal test level in a few cases, and many researches remain at a test tube level.

For example, JP-A-8-337536 discloses an anti-active oxygen agent extracted from a roasted and then fermented plant seed. The technique described in JP-A-8-337536 uses a plant seed as a starting material, but has low versatility because it requires operations such as roasting, fermentation treatment and the like, and, thus, this technique is not practical. In addition, no evidence exists that a fermented plant seed obtained by this method has an effect on suppressing atherosclerosis.

In another study, Zhang et al (Chem. Pharm. Bull., 45: pp 1910-14, 1997) report structures of a group of compounds extracted from a safflower oil cake by distribution of various solvents, and that some of these structures have an antioxidant activity in vitro. However, it is not clear at present if such compounds having an antioxidant activity are effective for preventing atherosclerosis. In consideration of the fact that antioxidant activity in vitro is known not to be necessarily correlated to the anti-atherosclerotic activity in living organisms (Fruebis et al, J. Lipid Res., 38: pp 2455-64, 1997, Fruebis et al, Atherosclerosis 117: pp 217-24, 1995, Munday et al, Arterioscler. Thromb. Vasc. Biol., 18: pp 114-19, 1998, Wagberg et al, J. Pharmacol. Exp. Ther., 299: pp 76-82, 2001), confirmation of whether or not an antioxidative substance in a plant seed has anti-atherosclerotic property is required at least at an experimental animal level.

Therefore, in view of the state of the art and the ever increasing medical concerns over atherosclerotic diseases, there remains a critical need for compositions that are effective atherosclerotic disease preventatives.

SUMMARY OF THE INVENTION

An object of the present invention is to provide a composition effective for preventing atherosclerosis, which is one of the lifestyle-related diseases. A further object of the present invention is to provide a food and a pharmaceutical composition containing this composition. In yet a further object of the present invention is to provide a method for preventing atherosclerosis.

The present inventors have conducted intensive studies to achieve the above-mentioned objects and have produced that a composition extracted with organic solvent from defatted plant seeds that has antioxidant activity in vitro and atherosclerosis preventive activity in experimental animals. On the basis of these findings, the present invention has been completed.

Thus, the present invention provides the following.

(1) A composition for preventing atherosclerosis, comprising an organic solvent extraction of a defatted plant seed.

(2) The composition of (1), wherein the plant seed is a seed of safflower.

(3) The composition of (1), wherein the plant seed is a seed of rapeseed.

(4) The composition of (1), wherein the organic solvent extraction is obtained by a process comprising extracting a defatted plant seed with a lower alcohol.

(5) The composition of (4), wherein said lower alcohol is ethanol or methanol.

(6) The composition of (4), wherein said process further comprises, after said extracting with a lower alcohol, evaporating said lower alcohol, adding water, extracting an aqueous phase, and washing said aqueous phase with a nonpolar solvent.

(7) The composition of (6), wherein said lower alcohol is ethanol or methanol.

(8) The composition of (4), wherein said process further comprises extracting with an acetate ester after said extracting with a lower alcohol.

(9) The composition of (8), wherein said acetate ester is selected from the group consisting of ethyl acetate, methyl acetate, and propyl acetate.

(10) The composition of (6), wherein said nonpolar solvent is n-hexane.

(11) The composition of (8), wherein said lower alcohol is ethanol or methanol.

(12) The composition of (8), wherein said process further comprises, after said extracting with a lower alcohol, evaporating said lower alcohol, adding water, extracting an aqueous phase, and washing said aqueous phase with a nonpolar solvent.

(13) The composition of (12), wherein said lower alcohol is ethanol or methanol.

(14) The composition of (12), wherein said acetate ester is selected from the group consisting of ethyl acetate, methyl acetate, and propyl acetate.

(15) The composition of (12), wherein said nonpolar solvent is n-hexane.

(16) A food comprising the composition of (1).

(17) A pharmaceutical composition comprising the composition of (1) and a pharmaceutically acceptable carrier.

(18) A method of preventing one or more atherosclerotic disease comprising administering to a subject in need thereof a composition of (1).

(19) The method of (18), wherein said atherosclerotic disease is one or more selected from the group consisting of angina pectoris, cardiac infarction, intermittent claudication, and cerebral infarction.

(20) The method of (18), wherein said effective amount ranges from 10 mg to 10 g per day.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 3 is a sketch for the purpose of clarifying the red stained part in FIG. 2 by drawing a figure of FIG. 2 and blacked out the red stained part.

DETAILED DESCRIPTION OF THE INVENTION

Figure 1:
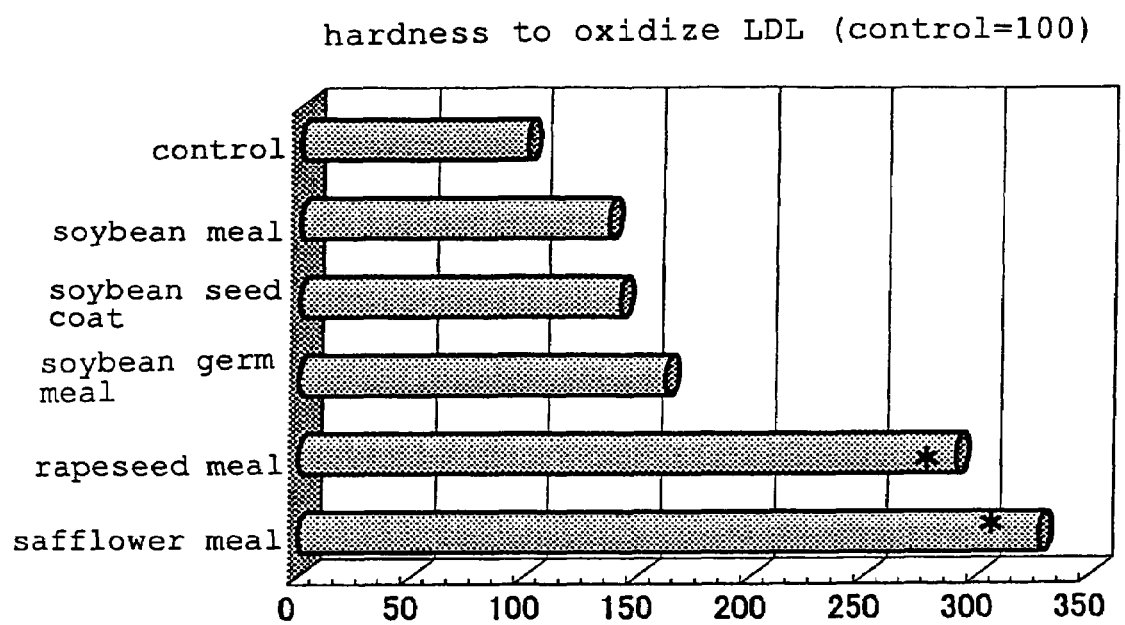
FIG. 1 shows the effect on LDL oxidation for each sample described in Example 1.

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The plant seed to be used in the present invention may be a seed of any plant. For example, seeds of safflower, rapeseed, soybean and the like can be mentioned, with preference given to the seeds of safflower and rapeseed. In the present invention, the term "plant seed" means the whole constituting a plant seed, or a part thereof, such as seed coat, albumen, germ and the like, or a mixture thereof.

In the present invention, the starting material is a plant seed after defatting or defatted material (meal). A defatted material of plant seed can be obtained by delipidating a plant seed by a method known per se. For example, the defatted material can be obtained by press-extracting seed or adding n-hexane and the like to a crushed seed, extracting the mixture, taking out a solid content from the extraction system and drying the solid content. The degree of defatting is generally not less than 60%, preferably not less than 80%.

The "organic solvent extraction" used in the present specification is explained below. Examples of the solvent to be used in the first step for extracting (e.g., organic solvent extraction) from defatted seed in the present invention include, but are not limited to, a lower alcohol (including water-containing lower alcohol), acetone (including water-containing acetone), acetonitrile (including water-containing acetonitrile), a mixed solvent thereof and the like. Preferably, the solvent for extraction is a lower alcohol. In this context, lower alcohol includes, for example, an alcohol having 1 to 4 carbon atoms. Specific examples thereof include, but are not limited to, methanol, ethanol, n-propanol, isopropanol, n-butanol and the like. The lower alcohol is preferably ethanol or methanol (including water-containing ethanol (e.g., 90 vol %) and water-containing methanol). A composition extracted with such solvent is useful as a composition of the present invention at a purity thereof, but may be processed to have a higher purity (may be purified).

One example for increasing the purity (purifying) is described in the following, but the method is not limited thereto. An organic solvent of the above-mentioned solvent extraction is evaporated (particularly evaporated under reduced pressure), water is added to the obtained extract to suspend the same, the suspension (aqueous phase) is washed with a nonpolar solvent (e.g., such as n-hexane, n-heptane, n-octane and the like, preferably n-hexane), and the aqueous layer after washing is extracted with a solvent that can extract an object composition in two separate layers (e.g., such as acetate ester, n-butanol and the like, preferably acetate ester, particularly preferably ethyl acetate, methyl acetate or propyl acetate). Then, the extract is washed with saturated brine and the like to produce an organic layer. When it is extracted with acetate ester, the organic layer is dehydrated over, for example, anhydrous magnesium sulfate and the like, and then concentrated under reduced pressure to give a solid (composition). Purification may be stopped during any of the above-mentioned steps. In addition, any step may be omitted or modified and the purification may be repeated or steps added thereto. A multi-step extraction method, a counter current distribution method and the like can be also used, including changing the kind of the above-mentioned solvent.

When the composition of the present invention obtained by the above-mentioned method is used as a food or a pharmaceutical agent (atherosclerosis preventive agent etc.), and/or when the composition is present in a physiologically harmful solvent, the composition may be dried, or the dry product is dissolved, suspended or emulsified in a physiologically acceptable solvent before use. The composition of the present invention may be in a liquid form (e.g., an aqueous solution and the like), a solid form obtained by concentration under reduced pressure and drying, or a solidified product such as a lyophilized product and the like.

The composition for preventing atherosclerosis of the present invention suppresses oxidation of LDL (low density lipoprotein) in human plasma in vitro. Particularly, a composition obtained from the seed of safflower and rapeseed strongly suppresses LDL oxidation. What is to be particularly noted is that the composition of the present invention suppresses formation of atheromatous plaque on an inner wall of the blood vessels in mouse in vivo and showed an anti-atherosclerotic activity in experimental animal. From the above, the composition of the present invention is useful as a pharmaceutical agent for prevention of atherosclerosis and the like, as well as a food for preventing atherosclerosis.

The composition of the present invention prevents atherosclerosis and is useful for preventing diseases caused by atherosclerosis, such as angina pectoris, cardiac infarction, intermittent claudication, cerebral infarction and the like.

The "food" of the present invention means food in general, and includes general food including health food, Food for Specified Health Use and Food with Nutrient Function Claims as defined in the Food with Health Claims System of the Health, Labor and Welfare Ministry, and encompasses supplements.

As the food or pharmaceutical composition, the above-mentioned composition of the present invention can be used may be used without further modification. In addition, it is possible to use the above-mentioned composition of the present invention contained in various foods. Examples of suitable foods include a general food (including what is called health food) such as dressing, mayonnaise and the like. Moreover, the composition of the present invention can be prepared into tablet, pill, granule, fine granules, powder, pellet, capsule, solution, emulsion, suspension, syrup, troche and the like together with excipients (e.g., lactose, sucrose, starch etc.), and with flavoring, dye and the like, and used as Food with Health Claims such as Food for Specified Health Use, Food with Nutrient Function Claims and the like, supplement, pharmaceutical preparation (pharmaceutical composition)(mainly for oral use).

Particularly, in the case of a pharmaceutical composition, the composition can be prepared along with a pharmaceutically acceptable carrier (including additive). Examples of the pharmaceutically acceptable carrier include, but not limited to, excipients (e.g., lactose, sucrose, starch, D-mannitol etc.), binders (e.g., cellulose, sucrose, dextrin, hydroxypropyl cellulose, polyvinylpyrrolidone etc.), disintegrants (e.g., starch, carboxymethyl cellulose etc.), lubricants (e.g., magnesium stearate etc.), surfactants (e.g., sodium lauryl sulfate etc.), solvents (e.g., water, brine, soybean oil etc.), preservatives (e.g., p-hydroxybenzoic acid ester etc.) and the like, which are known to those of ordinary skill in the art.

The intake amount and/or dose of the composition of the present invention for preventing atherosclerosis of the present invention varies depending on the purity of the composition, age, body weight and health condition of the subject and the like. However, the intake amount and/or dose is generally 10 mg-10 g, preferably 100 mg-10 g, is preferably given or administered to an adult per day for the prevention of atherosclerosis, which is given once a day or in several portions a day.

Since the composition of the present invention uses plant seeds which are conventionally used for food and the like (particularly, seed of safflower and rapeseed), which are used as a starting material of cooking oil, the toxicity is extremely low and side effects are scarcely observed.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

In Vitro Anti-Oxidation Data

Defatted safflower meal (100 g) was mixed with 500 ml of aqueous ethanol containing 90 vol % of ethanol and the mixture was warmed with stirring in a hot water bath at 60° C. for 3 hr. Subsequently, the mixture was filtered. After filtration, the process was repeated for the solid content and the obtained filtrates were combined and concentrated under reduced pressure to yield 60 ml of concentrated solution.

The volume of the concentrated solution was increased to 200 ml by suspending the contents of the concentrated solution in water. The suspension was then washed twice with 120 ml of n-hexane. After washing, the aqueous layer was extracted twice with ethyl acetate (100 ml). The ethyl acetate extract solution was washed with saturated brine, the ethyl acetate layer was dried over anhydrous magnesium sulfate, filtered and concentrated under reduced pressure to yield a solid (1.16 g).

Simultaneously, defatted rapeseed meal, soybean meal, soybean germ meal and soybean seed coat, respectively, were subjected to a similar treatment, 1 ml of DMSO was added to 1/10 amount of the above-listed extracts for dissolution and use as samples.

Plasma obtained from a human volunteer (adjusted to density=1.21 (g/ml) with KBr) was subjected to discontinuous density gradient centrifugation (417,000×g, 40 min, 4° C.)(OptimaTLX; Beckman Coulter) and an LDL band was withdrawn with a syringe. The protein content of the LDL fraction was measured (BCA protein assay kit; Pierce biotechnology, Inc.), and diluted with phosphate buffer (PBS) to a final concentration of 100 μg protein/ml. Thereto 1/100 amount of the above-mentioned sample was added followed by a radical initiator (V70; 2,2'-azobis(4-methoxy-2,4-dimethylvaleronitrile)) to a final concentration of 1 mM. The absorption at 234 nm (DU640; Beckman Coulter) based on the conjugated diene structure in lipid peroxide was immediately monitored for 5 hr. The lag time was calculated according to the method of Kondo et al. (J. Nutr. Sci. Vitaminol., 43: pp 435-44, 1997) based on the obtained lipid peroxide production curve. The effect of each sample on the oxidizability of LDL was evaluated by a relative value of the lag time with that of control (solvent alone was added) as 100 (FIG. 1). Every sample tended to more or less suppress oxidizability of LDL (i.e., extension of ragtime), but rapeseed meal and safflower meal were particularly strong suppressors of LDL oxidization.

The dilution fold of each sample before mixing with diluted human LDL in the above-mentioned test was 200-fold for rapeseed meal and safflower meal, and 50-fold for others. Since these meal extracts are liquid when converted to meal before extraction, rapeseed, and safflower meal extracts (200-fold diluted) were at 0.05 g/ml based on rapeseed meal and safflower meal, while soybean meal, soybean seed coat and soybean germ meal (50-fold diluted) were at 0.2 g/ml based on soybean meal, soybean seed coat and soybean germ meal. In other words, the rapeseed meal and safflower meal extract showed stronger antioxidant activity at a lower concentration.

Example 2

In Vivo Atherosclerosis Preventive Effect

Extracts of rapeseed meal and safflower meal were prepared as follows.

To defatted rapeseed meal (600 g) 3000 ml of aqueous ethanol containing 90 vol % of ethanol was added, and the mixture was warmed and stirred in a hot water bath at 60° C. for 3 hr, followed by filtration. This process was repeated with the solid content obtained after filtration and the resultant filtrates were combined and concentrated under reduced pressure to yield 500 ml of concentrated solution. Water was added to the concentrated solution to produce a suspension at a final volume of 1000 ml. The suspension was subsequently washed twice with 500 ml of n-hexane. The aqueous layer obtained after washing was extracted twice with ethyl acetate (500 ml) and the ethyl acetate extract solution was dried over anhydrous magnesium sulfate, filtered and concentrated under reduced pressure to yield an extract (12.5 g).

The defatted safflower meal (600 g) was treated in the same manner as described above resulting in 10.1 g of an extract.

Figure 2:
FIG. 2 shows the suppressive effect of a safflower meal extract composition and a rapeseed meal extract composition on atherosclerosis in the aorta of apoE (−/−) mice [atherosclerosis model mice] at week 5 of administration (14-week-old mice) as described in Example 2, wherein (a) is a control group, (b) is a safflower group and (c) is a rapeseed group.
Figure 2:
Figure 2:
Figure 3:
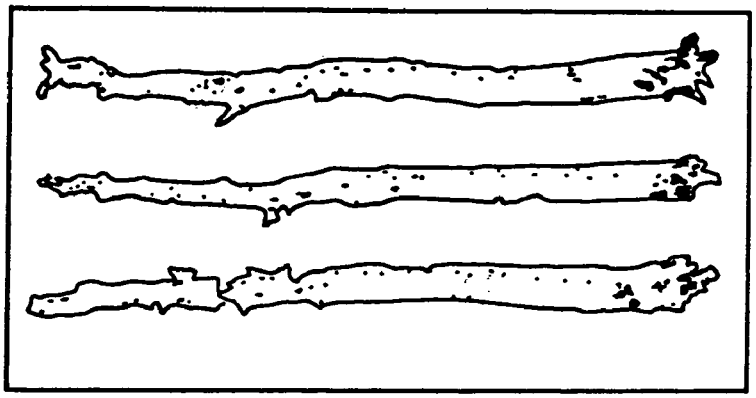
FIG. 3 shows a sketch of FIG. 2, wherein (a-1) is a sketch of FIG. 2(a), (b-1) is a sketch of FIG. 2(b), (c-1) is a sketch of FIG. 2(c). The photograph of FIG. 2 is originally a color photograph and the part stained in red shows an atheromatous plaque.
Figure 3:
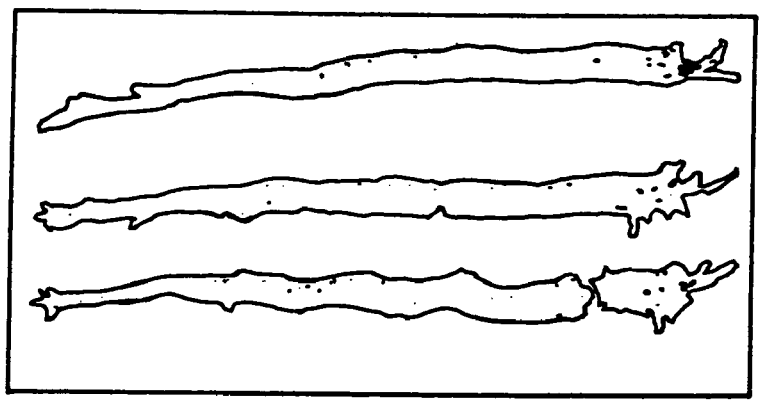
Figure 3:
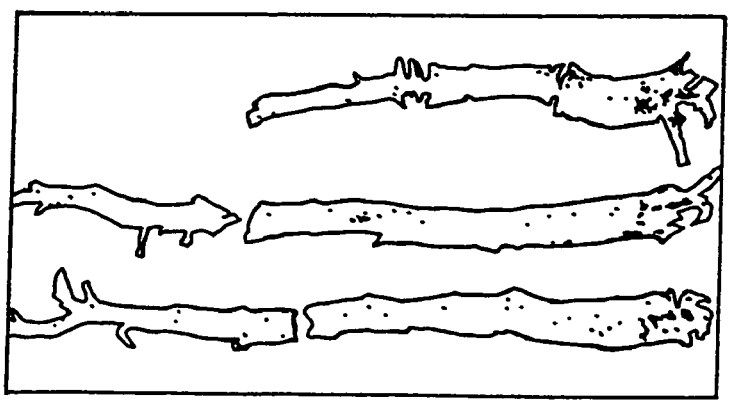

The 9-week-old male apoE knockout mice (apoE(-/-); purchased from The Jackson Laboratory) were divided into three groups of control/rapeseed (rapeseed meal extract administration group)/safflower (safflower meal extract administration group) with 9 mice per group, and each group was allowed free intake of a feed having ingredients shown in Table 1 for 5 weeks. The mice were killed at week 2 (n=6) and week 5 (n=3), a part of the aorta from the aortic root to the femoral artery bifurcation was removed, and the area of atheromatous plaque (plaque) formed on the vascular inner wall stained with Sudan IV was compared with that of the control group. By 2 weeks' administration, plaque formation tended to be suppressed in the rapeseed group and safflower group as compared to the control group. By comparison of groups after extended administration for 3 weeks thereafter, the above-mentioned tendency became stronger (plaque area: safflower<rapeseed<control), and an effect of suppressing formation of initial lesion of atherosclerosis was exhibited by these oil plant meal extracts (FIG. 2 and FIG. 3).

Figure 4:
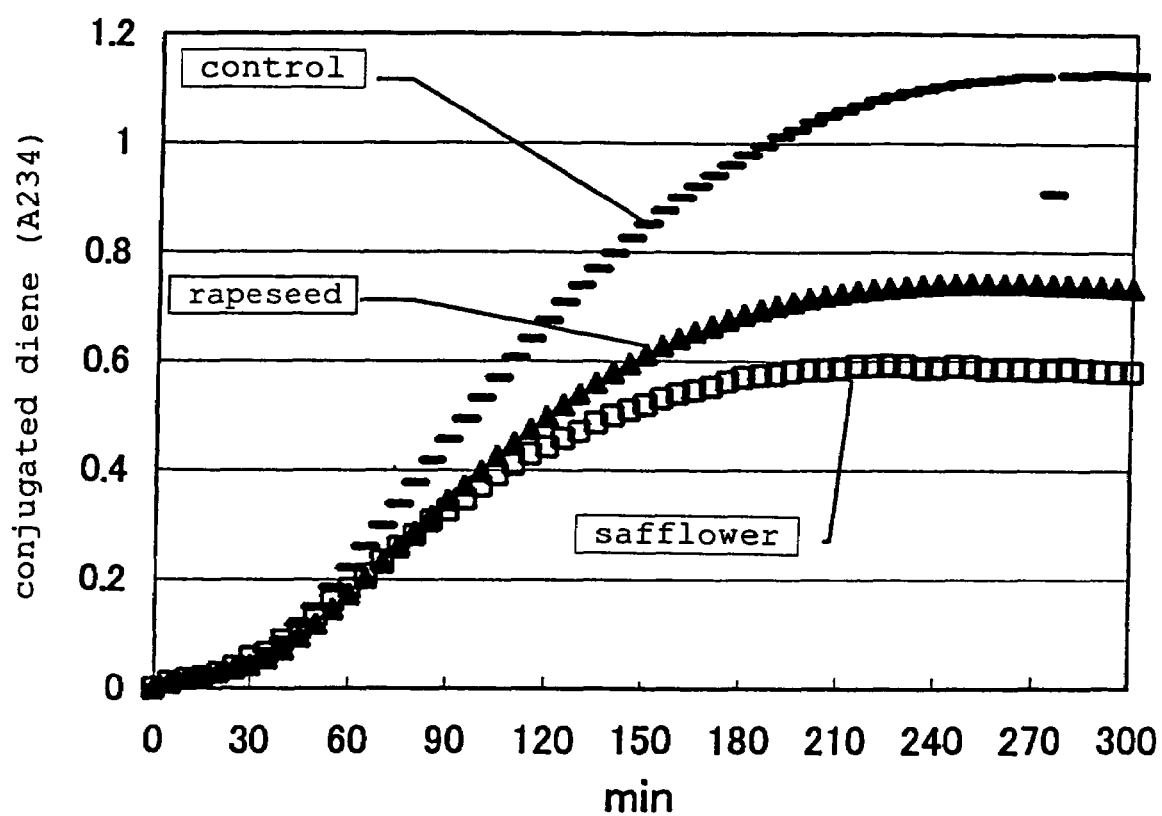
FIG. 4 shows an oxidation curve of LDL induced by the addition of V70 (lipid peroxide producing curve).

Blood was taken from the abdominal vena cava of the mouse killed in the above-mentioned test. Plasma (adjusted to density of 1.30 (g/ml) with KBr), separated according to conventional methods, was subjected to discontinuous density gradient centrifugation (417,000×g, 1 hr, 4° C.)(Optima TLX; Beckman Coulter) and a lipoprotein fraction was fractionated using a fractionator (DGF-U; Hitachi Koki Co., Ltd.). The protein content of the VLDL (very low density lipoprotein)—LDL (low density lipoprotein) fraction of each group, confirmed by electrophoresis (Multigel-lipo; Daiichi Pure Chemicals Co., Ltd), was measured (BCA protein assay kit; Pierce Biotechnology, Inc.). Subsequently, the fraction was diluted with phosphate buffer (PBS) to a final concentration of 50 µg protein/ml, a radical initiator (V70; 2,2'-azobis(4-methoxy-2,4-dimethyl valeronitrile)) was added to a final concentration of 250 µM, and the absorption at 234 nm (DU-640; Beckman Coulter) based on the conjugated diene structure in lipid peroxide at 37° C. was immediately initiated. A lipid peroxide production curve was plotted for each of the administration group and the control group. The production rate and the amount of product were compared (FIG. 4).

Based on the foregoing, it was determined that the lipoprotein fractions of the rapeseed and safflower administration groups showed lesser accumulation of lipid peroxide as compared to the control group (namely, less easily oxidized) (safflower<rapeseed<control).

TABLE 1

| group | Ingredients of feed |
| --- | --- |
| control | Normal diet (20% (w/w) vitamin-free casein, 66.3% starch, 5% corn oil, 3.5% AIN-93-mineral mixture, 1% AIN-93-vitamin mixture, 0.2% choline chloride, 4% cellulose powder) |
| rapeseed | Normal diet + 1.3% (w/w) rapeseed meal extract* |
| safflower | Normal diet + 1.0% (w/w) safflower meal extract* |

*balanced with starch

Example 3

6-7-week-old male apoE knockout mice (purchased from The Jackson Laboratory) were divided into 5 groups: (a) control (Control), (b) serotonin derivative 0.2 wt % administration (p-coumaroylserotonin (CS), feruloylserotonin (FS), 0.1% each) (CS+FS, 0.2%), (c) serotonin derivative 0.4 wt % administration (p-coumaroylserotonin (CS), feruloylserotonin (FS), 0.2% each) (CS+FS, 0.4%), (d) feruloylserotonin (FS) 0.4 wt % administration (FS, 0.4%), and (e) safflower meal extract (SFM) 1 wt % administration (SFM, 1%) with 7-10 mice per group. Each group was allowed free intake of a feed having ingredients shown in Table 2 for 15 weeks.

Figure 5:
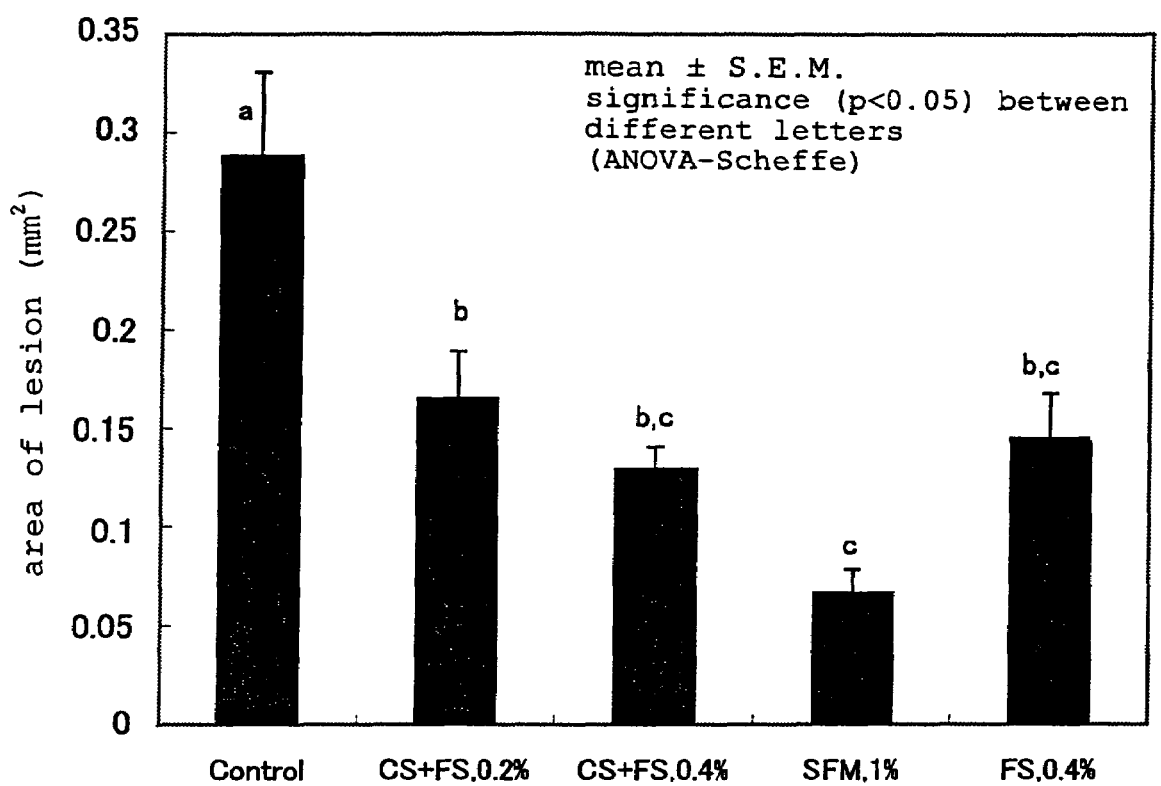
FIG. 5 shows an aortic root lesion area in apoE knockout mice (21-week-old, male, week 15 of administration of each sample) as described in Example 3, wherein SFM is a safflower meal extract composition, CS is p-coumaroylserotonin and FS is feruloylserotonin.

The safflower meal extract (SFM) used in this Example was prepared according to the method described in Example 2. After completion of the administration period, the mice were killed, the aortic root was sliced and the lipid deposition part (atherosclerosis lesion) was stained with Oil Red O. Three slices were prepared for one individual and the samples most clearly showing the aortic valve were subjected to image analysis (using WinROOF (MITANI CORPORATION)) and the area of the lesion was measured based on the method of Rajendra et al (J. Lipid Res., 36: pp 2320-2328, 1995). The obtained area of the lesion was subjected to an analysis of variance between respective groups, and when a significant difference was observed, the average values were compared between groups by the Scheffe test. While a serotonin derivative (Zhang et al, Chem. Pharm. Bull., 44: pp 874-876,1996, Kawashima et al, J. Interferon Cytokine Res., 18: pp 423-428, 1998), which is a main phenolic substance in safflower meal known to have antioxidant activity and anti-inflammatory activity in vitro, partially suppressed lesion formation in apoE knockout mice, a safflower meal extract (SFM, containing 10-30 wt % of serotonin derivative) was found to suppress stronger than that (FIG. 5).

TABLE 2

| composition | Control | CS + FS, 0.2% | CS + FS, 0.4% | SFM, 1% | FS, 0.4% |
|---|---|---|---|---|---|
| | | g (in 1 kg of diet) | | | |
| vitamin-free casein | 200.0 | 200.0 | 200.0 | 200.0 | 200.0 |
| corn starch | 632.5 | 630.5 | 628.5 | 622.5 | 628.5 |
| corn oil | 70.0 | 70.0 | 70.0 | 70.0 | 70.0 |
| mineral mixture (AIN-93G) | 35.0 | 35.0 | 35.0 | 35.0 | 35.0 |
| vitamin mixture (AIN-93G) | 10.0 | 10.0 | 10.0 | 10.0 | 10.0 |
| choline tartrate | 2.5 | 2.5 | 2.5 | 2.5 | 2.5 |
| cellulose powder | 50.0 | 50.0 | 50.0 | 50.0 | 50.0 |
| p-coumaroyl-serotonin | 0.0 | 1.0 | 2.0 | 0.0 | 0.0 |
| Feruloyl-serotonin | 0.0 | 1.0 | 2.0 | 0.0 | 4.0 |
| safflower meal extract | 0.0 | 0.0 | 0.0 | 10.0 | 0.0 |
| total | 1000.0 | 1000.0 | 1000.0 | 1000.0 | 1000.0 |

Since the composition of the present invention, which is obtained by organic solvent extraction of defatted plant seed, is a naturally occurring material it, shows high safety and almost no side effects. As such, based on the results demonstrated above, the resultant composition of the present invention is an effective preventative of atherosclerosis. Further, a food and a pharmaceutical composition containing the composition are also effective for preventing atherosclerosis.

Numerous modifications and variations on the present invention are possible in light of the above teachings. It is, therefore, to be understood that within the scope of the accompanying claims, the invention may be practiced otherwise than as specifically described herein.

The invention claimed is:

1. A composition for inhibiting plaque formation, comprising an organic solvent extraction of a safflower plant seed, wherein the organic solvent extraction is obtained by a process comprising extracting a defatted plant seed with ethanol, after said extracting with ethanol, evaporating said ethanol, adding water, extracting an aqueous phase, and washing said aqueous phase with a nonpolar solvent and wherein the organic solvent extraction comprises p-coumaroyl serotonin and/or feruloyl serotonin as an active ingredient.

2. The composition of claim 1, wherein said nonpolar solvent is n-hexane.

3. A food comprising the composition of claim 1.

4. A pharmaceutical composition comprising the composition of claim 1 and a pharmaceutically acceptable carrier.

5. The composition of claim 1, wherein said process further comprises extracting with an acetate ester after said extracting and washing said aqueous phase with a nonpolar solvent.

6. The composition of claim 5, wherein said acetate ester is selected from the group consisting of ethyl acetate, methyl acetate, and propyl acetate.

7. The composition of claim 5, wherein said nonpolar solvent is n-hexane.

8. The composition of claim 1, wherein said p-coumaroyl serotonin and/or feruloyl serotonin is present at a concentration of 10-30 wt %.

9. A composition for inhibiting plaque formation, comprising an organic solvent extraction of a safflower plant seed, wherein the organic solvent extraction is obtained by a process consisting essentially of extracting a defatted plant seed with ethanol and extracting with an acetate ester after said extracting with ethanol, and wherein the organic solvent extraction comprises p-coumaroyl serotonin and/or feruloyl serotonin as an active ingredient.

10. The composition of claim 9, wherein said acetate ester is selected from the group consisting of ethyl acetate, methyl acetate, and propyl acetate.

* * * * *